United States Patent [19]

Lim et al.

[11] Patent Number: 5,409,830
[45] Date of Patent: Apr. 25, 1995

[54] METHOD FOR PRODUCTION OF L-PHENYLALANINE BY ECHERICHIA COLI MUTANT THAT IS RESISTANT TO OSMOTIC PRESSURE

[75] Inventors: Byung L. Lim; Hong Rhym; Jin H. Lee; Tae Y. Choi; E. Nam Hwang; Hong K. Choi, all of Seoul, Rep. of Korea

[73] Assignee: Miwon Co. Ltd., Seoul, Rep. of Korea

[21] Appl. No.: 263,493

[22] Filed: Jun. 21, 1994

Related U.S. Application Data

[63] Continuation of Ser. No. 991,172, Dec. 16, 1992, abandoned.

[51] Int. Cl.6 .................... C12P 13/22; C12N 1/20
[52] U.S. Cl. .................... 435/252.8; 435/108; 435/849
[58] Field of Search .............. 435/108, 252.8, 252.33

[56] References Cited

U.S. PATENT DOCUMENTS 4,681,852  7/1987  Tribe et al. ............... 435/172.3

FOREIGN PATENT DOCUMENTS 376345    6/1962   Japan .
55-165797 12/1980  Japan .
60-160890 8/1985   Japan .

Primary Examiner—Marian Knode
Attorney, Agent, or Firm—Birch, Stewart, Kolasch & Birch

[57] ABSTRACT

A novel E. coli strain which can produce L-phenylalanine and is resistant to high osmotic pressure and a process for producing L-phenylalanine by use of the novel E. coli (KCCM 10,016) are disclosed.

2 Claims, No Drawings

METHOD FOR PRODUCTION OF L-PHENYLALANINE BY *ECHERICHIA COLI* MUTANT THAT IS RESISTANT TO OSMOTIC PRESSURE

This application is a continuation of application Ser. No. 07/991,172, filed on Dec. 16, 1992, now abandoned.

BACKGROUND OF THE INVENTION

1. Field of the Invention

The present invention relates to a method for production of L-phenylalanine by *Escherichia coli* (hereinafter *E. coli*) which is resistant to high osmotic pressure and produces L-phenylalanine in a high yield.

2. Description of Related Art

L-phenylalanine is an essential amino acid and can be used for the synthetic production of ASPARTAME ®, a sweetening agent. There are many known methods for production of L-phenylalanine by use of microbes. For example, Japanese Patent No. 37-6345 and Japanese Kokai No. 60-160,890 disclose a method for production of L-phenylalanine by use of Brevibacterium and Corynebacterium species which require tyrosine. Japanese Kokai 55-165,797 discloses a similar method by use of an *E. coli* which requires tyrosine and which is resistant to tryptophan analogues and phenylalanine analogues. However, such related art processes are not particularly suited for L-phenylalanine production on an industrial scale; these processes produce low yields of L-phenylalanine.

SUMMARY OF THE INVENTION

Accordingly, it is an object of the present invention to provide a method for production of L-phenylalanine, which eliminates the above problems encountered with conventional processes.

Another object of the present invention is to provide a process for the preparation of L-phenylalanine, which comprises culturing *E. coli* in a culture medium, aerating and agitating the culture medium and recovering L-phenylalanine from the culture medium.

A further object of the present invention is to provide a novel *E. coli* (KCCM 10,016) having tolerance against osmotic pressure during culture using sorbitol or sodium chloride.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Referring now in detail to the present invention, there is provided a method for obtaining a novel *E. coli* producing L-phenylalanine at high concentration in a culture medium and a process for the preparation of L-phenylalanine from a microbial fermentation broth by use of such a novel microbe.

In general, since L-phenylalanine has an aromatic ring in its formula, it is difficult to obtain a high yield of this amino acid from metabolic synthetic processes.

The novel microbe, *Escherichia coli* MWOR 247, (deposited under the accession number KCCM 10,016 on Oct. 22, 1992 at the Korean Culture Center of Microorganisms, Department of Food Engineering, College of Eng. Yonsei University, sodaemun-gu, Seoul 120-749, Korea), according to the present invention is improved from *E. coli* MWWJ 304 (KFCC 10737). *E. coli* MWWJ 304 (KFCC 10,737) is the parent strain of *E. coli* MWOR 247 (KCCM 10,016) and was deposited on Aug. 30, 1991 at the Korean Federation of Culture Collections, Department of Food Engineering, College of Engineering, Yonsei University, Seoul, Korea. The *E. coli* MWWJ 304 is a strain resistant to analogs of L-phenylalanine and L-tyrosine, and further harbors a temperature-sensitive, leaky auxotrophy for L-tyrosine. The *E. coli* MWWJ 304 has a number of disadvantages, for example, the rate of production of L-phenylalanine decreases as the concentration of L-phenylalanine reaches more than 30 g/l in a terminal fermentation. Also, the production of L-phenylalanine is unstable due to loss of plasmid DNA from this transformant during fermentation.

It is believed that the above problems caused by use of *E. coli* strain MWWJ 304 are solved as follows. That is, osmotic pressure is increased in the culture during fermentation as the concentration of L-phenylalanine increases. The increase in osmotic pressure in turn causes the reduction in the production of L-phenylalanine by the cells.

Accordingly, the novel microbe, *E. coli* MWOR 247 (KCCM 10,016), increases the productivity of L-phenylalanine under conditions of a gradually increasing osmotic pressure in the culture. That is, the *E. coli* MWOR 247 has a number of advantages as follows when compared with the *E. coli* MWWJ 304:

(a) The growth is very good even if an excess of sorbitol or sodium chloride is added to the cultivation.

(b) The productivity of L-phenylalanine does not decrease even though a high concentration of L-phenylalanine is accumulated in the culture.

DETAILED DESCRIPTION OF THE INVENTION

Referring now in more detail to the present invention, there is provided a process for the preparation of L-phenylalanine.

After the original parent strain, *E. coli* MWWJ 304, is incubated in culture medium No. 1 at a temperature of about 37° C. for 16–18 hours, one loopful of the culture is inoculated into 10 ml of culture medium No. 2 at a temperature of 37° C. for 4–6 hours and is centrifuged to collect the cells.

Thereafter, the collected cells are washed with saline solution and suspended in 8 ml of 0.1M of tris-maleate buffer solution (pH 6.0). 2 ml of 100 $\mu$g/ml concentration of N-methyl-N[1]-nitro-N-nitrosoguanidine is added to 8 ml of the above suspension. After the suspension is shaken reciprocally at a temperature of about 37° C. for 30 minutes, the cells are isolated from the suspension by centrifugation and washed. The strain is cultured in the culture medium No. 3 at a temperature of about 37° C. for 48 hours. At this time, *E. coli* MWOR strain are obtained by selecting colony growing on the culture medium No. 3.

The novel strain, *E. coli* MWOR 247 of the present invention exhibits physiological characteristics and L- phenylalanine productivity as follows when compared with the parent strain *E. coli* MWWJ 304:

(1) Comparison of Growth with Added Sodium Chloride or Sorbitol

After sodium chloride or sorbitol is added to culture medium No. 4, 40 ml of the culture is charged into a 500 ml shaking flask. 1 ml of cells grown at 37° C. for 4–6 hours in culture medium No. 2 is added to the flask and are grown with reciprocal shaking at a temperature of about 37° C. for 24 hours. Thereafter, a sample of the culture is diluted about 10-fold and the absorbance is measured at 610 nm as the following Table I:

TABLE I

Comparison of growth with added sodium chloride or sorbitol

| | Strain | |
|---|---|---|
| Additive | *E. coli* MWWJ304 | *E. coli* MWOR247 |
| No addition | 0.328 | 0.315 |
| Sodium Chloride 9/l | 0.124 | 0.295 |
| Sodium Chloride 18 g/l | 0.027 | 0.220 |
| Sorbitol 55 g/l | 0.141 | 0.289 |
| Sorbitol 110 g/l | 0.032 | 0.234 |

(2) Comparison of Growth with Added L-phenylalanine

After L-phenylalanine is added to the culture medium No. 4, 40 ml of the medium is charged into a 500 ml shaking flask. As in the above described method, 1 ml of cells subcultured in culture medium No. 2 at 37° C. for 4–6 hours is added to the flask and the cells are grown with reciprocal shaking at 37° C. for 24 hours. Thereafter, samples of the culture are diluted about 10-fold and the absorbance is measured at 610 nm. Results are shown in the following Table II:

TABLE II

Comparison of growth with added L-phenylalanine

| | Strain | |
|---|---|---|
| L-Phe (g/l) | *E. coli* MWWJ304 $A_{610} \times 10^{-1}$ | *E. coli* MWOR247 $A_{610} \times 10^{-1}$ |
| 0 | 0.328 | 0.315 |
| 5 | 0.119 | 0.303 |
| 10 | 0.033 | 0.276 |
| 20 | 0.017 | 0.241 |

(3) Production of L-phenylalanine

After preparing culture medium No. 5, 40 ml of the medium is charged into a 500 ml shaking flask. As in the above-described method, 1 ml of cells subcultured in culture medium No. 2 at 37° C. for 4–6 hours is added to the flask and the cells are grown with reciprocal shaking at 37° C. for 48 hours. After 2 ml of 60% glucose is added to the culture medium, the culture is continued for 24 hours. The amount of L-phenylalanine in the culture broth is assayed by a conventional method using High Performance Liquid Chromatography. Results are shown as the following Table III:

TABLE III

Productivities of L-phenylalanine

| | Strain | |
|---|---|---|
| Culture time (hr.) | *E. coli* MWWJ304 | *E. coli* MWOR247 |
| 48 | 20.1 | 20.6 |
| 72 | 22.7 | 27.6 |

(4) Comparison of Growth and L-phenylalanine Production of Successively Subcultured *E. coli* MWOR247

After the novel strain, *E. coli* MWOR247, is incubated in the culture medium No. 1 at a temperature of about 37° C. for 24 hours. One loopful of the cultured cells is inoculated into fresh culture medium No. 1. The culture is incubated at about 37° C. for 24 hours. As in the above description, the inoculation and incubation is repeated serially for 30 times. During the first, 10th, 20th, and 30th subculturings, the strain is tested according to the method of the above-described Example (3), Production of L-Phenylalanine, and also the culture is diluted 50-fold and the absorbance is measured at 610 nm. Results are shown in the following Table IV:

TABLE IV

Growth and L-phenylalanine production of *E. coli* MWOR 247 subcultured daily for 30 days

| | Culture Time | | | |
|---|---|---|---|---|
| Subculture passage | 48 hours | | 72 hours | |
| | growth | L-Phe g/l | growth | L-Phe g/l |
| 1 | 0.712 | 20.6 | 0.732 | 27.6 |
| 10 | 0.730 | 19.9 | 0.741 | 26.8 |
| 20 | 0.694 | 20.5 | 0.728 | 27.1 |
| 30 | 0.709 | 20.7 | 0.719 | 27.5 |

The composition of the culture media recited in the above Examples are as follows:

| (A) | Culture Medium No. 1 | |
|---|---|---|
| | Bacto yeast Extract | 5 g/l |
| | Tryptone | 10 g/l |
| | Sodium Chloride | 10 g/l |
| | Agar | 20 g/l |
| | (pH 7.5, Sterilized at 121° C. for 15 min.) | |
| (B) | Culture Medium No. 2 | |
| | Bacto yeast Extract | 5 g/l |
| | Tryptone | 10 g/l |
| | Sodium Chloride | 10 g/l |
| (C) | Culture Medium No. 3 | |
| | Glucose | 2 g/l |
| | Sodium Phosphate, dibasic | 6 g/l |
| | Potassium Phosphate, monobasic | 3 g/l |
| | Sodium Chloride | 0.5 g/l |
| | Ammonium Chloride | 1 g/l |
| | Magnesium Sulfate | 0.2 g/l |
| | Calcium Chloride | 0.01 g/l |
| | L-Tyrosine | 0.02 g/l |
| | Sorbitol | 110 g/l |
| | Agar | 20 g/l |
| | (pH 7.0, sterilized at 121° C. for 15 min) | |
| (D) | Culture Medium No. 4 | |
| | Glucose | 2 g/l |
| | Sodium Phosphate, dibasic | 6 g/l |
| | Potassium Phosphate, monobasic | 3 g/l |
| | Sodium Chloride | 0.5 g/l |
| | Ammonium Chloride | 1 g/l |
| | Magnesium Sulfate | 0.2 g/l |
| | Calcium Chloride | 0.01 g/l |
| | L-Tyrosine | 0.02 g/l |
| (E) | Culture Medium No. 5 | |
| | Glucose | 80 g/l |
| | Potassium Sulfate | 0.5 g/l |
| | Ammonium Sulfate | 20 g/l |
| | Sodium Citrate | 0.5 g/l |
| | Fumaric Acid | 0.5 g/l |
| | Magnesium Chloride | 1 g/l |
| | Potassium Phosphate, monobasic | 1 g/l |
| | Potassium Phosphate, dibasic | 1 g/l |
| | Yeast Extract | 1 g/l |

| | |
|---|---|
| Glutamic Acid | 0.5 g/l |
| Cobalt Chloride | 0.1 mg/l |
| Zinc Sulfate | 1 mg/l |
| Manganese Chloride | 2 mg/l |
| Calcium Chloride | 5 mg/l |
| Ferric Chloride | 20 mg/l |
| L-Tyrosine | 200 mg/l |
| Calcium Carbonate* (pH 7.5, sterilized at 121° C. for 15 min) | 35 g/l |

*sterilized separately

Accordingly, the novel microbe, MWOR 247, exhibits excellent growth in media containing excess sorbitol, sodium chloride or L-phenylalanine. The novel strain also displays excellent productivity in the high concentration L-phenylalanine accumulated at the end period of the cultivation as compared with the parent strain, MWWJ304. Also, in the serially subcultured method, the growth and productivity are excellent.

Furthermore, the novel microbe, MWOR247 of the present invention does not require any plasmid to maintain its excellent phenylalanine productivity. The strain is an overproducer of phenylalanine as a result of a chromosomal mutation, strain MWOR 247 harbors no extrachromosomal DNA. Thus, overproduction of phenylalanine by strain MWOR 247 is not plasmid dependent and the strain does not suffer from instability of phenylalanine production due to loss of plasmid DNA during culture. In contrast, the parent strain, MWWJ304 requires induction of gene expression from a plasmid to improve L-phenylalanine production.

According to the present invention, L-phenylalanine is produced by cultivating the novel strain, MWOR247 in a culture medium containing carbon, nitrogen, inorganic salts and organic nutrition sources. Thereafter, the culture medium accumulates L-phenylalanine, which is purified from the medium by conventional ion-exchange resin, decolored by means of the conventional method, and concentrated so as to produce purified L-phenylalanine.

The present invention will now be described in more detail in connection with the following examples which should be considered as being exemplary and not limiting of the present invention.

EXAMPLE 1

Inoculation medium is the above culture medium No. 2 and culture medium is the above culture medium No. 5.

40 ml of the inoculation medium is charged into a 500 ml shaking flask and heated at 121° C. for 15 minutes so as to sterilize it. The novel *E. coli* strain MWOR 247 (KCCM 10,016) is added to the flask and cultivated at 37° C. for 8–10 hours to produce an inoculum culture.

40 ml of the culture medium is charged into a 500 ml shaking flask and sterilized the same as the above method. At this time, 1 ml of the inoculum culture is added to the above sterilized culture media in the flask and the culture is incubated for 48 hours with reciprocal shaking. Then 2 ml of 60% of glucose is added to the culture medium and the incubation is continued with reciprocal shaking for 24 hours. The accumulated amount of L-phenylalanine is 27.6 g/l.

EXAMPLE 2

Cells of strain *E. coli* MWOR 247 (KCCM 10,016) are inoculatd in culture medium No. 5, except that calcium carbonate is omitted and the glucose concentration is 100 g/l. One liter of this culture medium is charged into a 2 l fermentation reactor. 40 ml of the inoculum culture prepared as in Example 1 is added to the fermentation reactor and cultured under 1,000 rpm and 0.75 vvm air at 37° C. for 45 hours. During the culture, the pH is maintained at 7.0 by addition of ammonia and when the residual glucose concentration is 1%, 60 ml of 60% of glucose is added to the fermention reactor. The total amount of glucose used is 170.5 g and the amount of L-phenylalanine finally accumulated is 44.3 g/l. 1 liter of cell-free culture medium is treated by the conventional method to produce 39.9 grams of L-phenylalanine.

EXAMPLE 3

20 liters of the culture medium of Example 2 is charged into a 50 liter fermentation reactor and sterilized at 121° C. for 15 minutes. Thereafter, a scaled-up culture, made as in Example 2, with the exception that 60 ml of 60% glucose is added to the fermentation reactor six times, is performed. 207.4 g/l of sugar is used and the finally accumulated amount of L-phenylalanine is 48.7 g/l.

The invention being thus described, it will be obvious that the same may be varied in many ways. Such variations are not to be regarded as a departure from the spirit and scope of the invention, and all such modifications as would be obvious to one skilled in the art are intended to be included in the scope of the invention as set forth in the following claims.

What is claimed is:

1. A biologically pure culture of *Escherichia coli* having all the identifying characteristics of *Escherichia coli* MWOR 247.

2. The biologically pure culture of claim 1 wherein said *Escherichia coli* is *Escherichia coli* MWOR 247.

* * * * *